United States Patent
Sinclair et al.

(10) Patent No.: US 9,574,285 B2
(45) Date of Patent: Feb. 21, 2017

(54) APPARATUS AND METHOD FOR MONITORING AND CONTROLLING THICKNESS OF A CRYSTALLINE LAYER

(71) Applicant: Varian Semiconductor Equipment Associates, Inc., Gloucester, MA (US)

(72) Inventors: Frank Sinclair, Quincy, MA (US); Peter L. Kellerman, Essex, MA (US)

(73) Assignee: Varian Semiconductor Equipment Associates, Inc., Gloucester, MA (US)

( * ) Notice: Subject to any disclaimer, the term of this patent is extended or adjusted under 35 U.S.C. 154(b) by 246 days.

(21) Appl. No.: 14/566,085

(22) Filed: Dec. 10, 2014

(65) Prior Publication Data

US 2016/0168748 A1    Jun. 16, 2016

(51) Int. Cl.
*C30B 29/02* (2006.01)
*C30B 15/26* (2006.01)
*C30B 15/06* (2006.01)
*C30B 29/06* (2006.01)

(52) U.S. Cl.
CPC ............... *C30B 15/26* (2013.01); *C30B 15/06* (2013.01); *C30B 29/06* (2013.01)

(58) Field of Classification Search
CPC ........... C30B 15/02; C30B 15/06; C30B 15/22
See application file for complete search history.

(56) References Cited

U.S. PATENT DOCUMENTS

| | | | | |
|---|---|---|---|---|
| 6,077,345 A | * | 6/2000 | Easoz | C30B 15/02 117/14 |
| 6,187,090 B1 | * | 2/2001 | Maeda | C30B 15/22 117/14 |
| 6,241,818 B1 | * | 6/2001 | Kimbel | C30B 15/20 117/13 |
| 6,471,768 B2 | * | 10/2002 | Terao | C30B 15/26 117/16 |
| 7,326,292 B2 | * | 2/2008 | Kim | C30B 15/26 117/14 |
| 8,475,591 B2 | | 7/2013 | Kellerman et al. | |
| 2012/0210931 A1 | * | 8/2012 | Bender | C30B 15/02 117/15 |

OTHER PUBLICATIONS

Kellerman, Peter L., et al., Apparatus for controlling heat flow within a silicon melt, filed Mar. 27, 2014 as U.S. Appl. No. 14/227,005.

(Continued)

*Primary Examiner* — Robert M Kunemund

(57) ABSTRACT

An apparatus to monitor thickness of a crystalline sheet grown from a melt. The apparatus may include a process chamber configured to house the melt and crystalline sheet; an x-ray source disposed on a first side of the crystalline sheet and configured to deliver a first beam of x-rays that penetrate the crystalline sheet from a first surface to a second surface opposite the first surface, at a first angle of incidence with respect to the first surface; and an x-ray detector disposed on the first side of the crystalline sheet and configured to intercept a second beam of x-rays that are generated by reflection of the first beam of x-rays from the crystalline sheet at an angle of reflection with respect to the first surface, wherein a sum of the angle of incidence and the angle of reflection satisfies the equation $\lambda = 2d \sin \theta$.

20 Claims, 7 Drawing Sheets

(56) References Cited

OTHER PUBLICATIONS

Carlson, Frederick M., Apparatus for processing a melt, filed May 12, 2014 as U.S. Appl. No. 14/275,770.
Kellerman, Peter L., et al., Apparatus and method for controlling thickness of a crystalline sheet grown on a melt, filed Oct. 17, 2014 as U.S. Appl. No. 14/517,217.
Chikawa, Jun-Ichi Live X-ray topography and crystal growth of silicone, Japan Journal of Applied Physics, Aug. 1999, pp. 4519-4631, vol. 39, Part 1, No. 8, Publication Board Japanese Journal of Applied Physics.

* cited by examiner

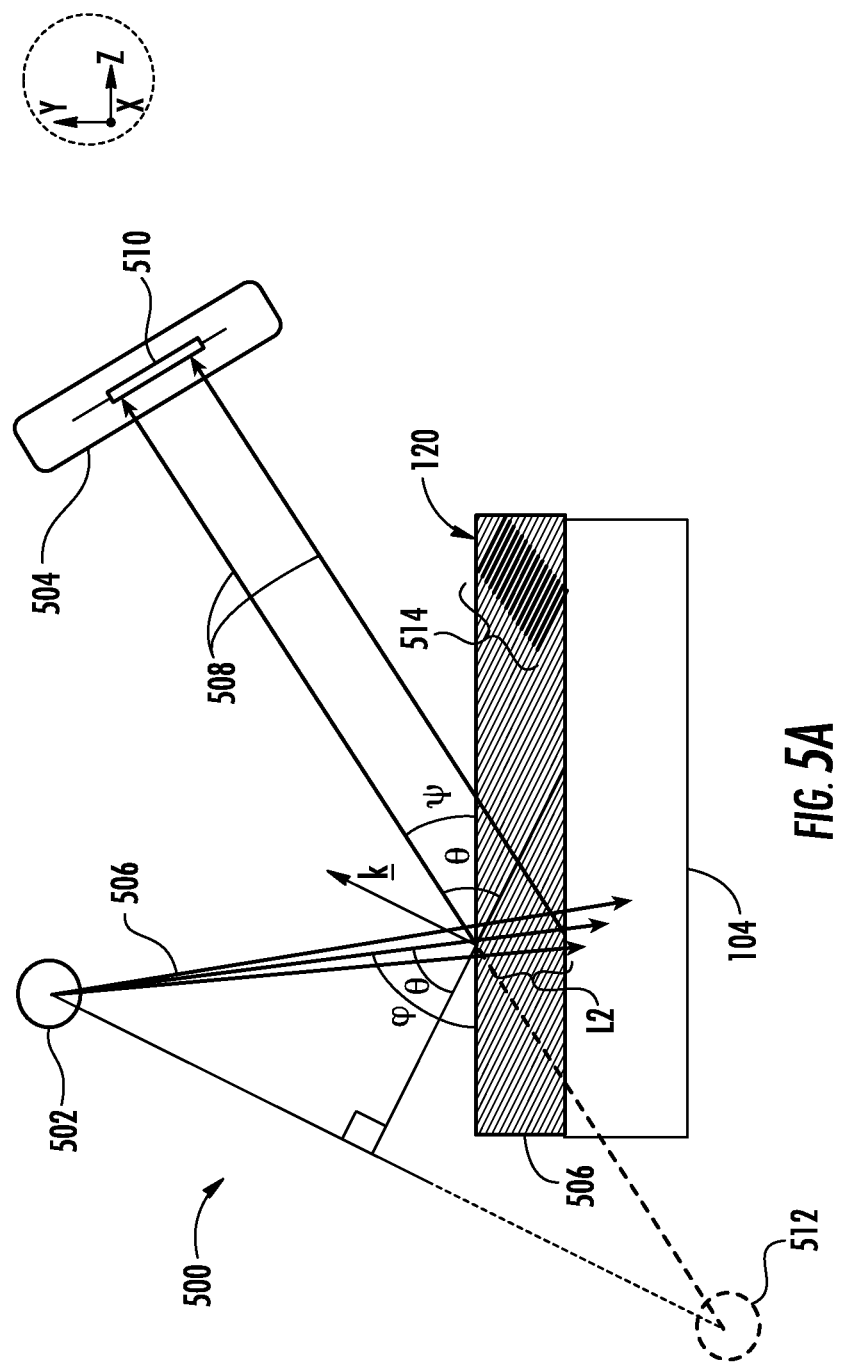

APPARATUS AND METHOD FOR MONITORING AND CONTROLLING THICKNESS OF A CRYSTALLINE LAYER

FIELD

The present embodiments relate to measurement of monocrystalline layers and in particular to apparatus and techniques for controlling thickness of crystalline material grown from a melt.

BACKGROUND

In the present day various apparatus are available to measure thickness of crystalline layers that may be free standing or disposed on a substrate. Although many techniques are available to measure a crystalline layer in a static fashion, such as when the layer is disposed on a substrate at room temperature, measurement of layer thickness during formation of a crystalline layer may be more challenging. This is especially so when growth takes place under elevated temperature or under special ambient.

In the present day techniques have been developed to grow single crystalline (monocrystalline) sheets from a melt of a given material such as silicon or sapphire. This may be accomplished by crystallizing a thin solid layer of the given material on the surface of a melt and drawing an edge of the layer along the melt or pulling the layer from the melt according to known techniques. Control of the crystallinity and thickness of such monocrystalline sheets may depend upon a number of factors, including growth temperature, pulling rate, and so forth. Accordingly, precise control of growth parameters may be desirable. Moreover, it may be desirable to measure properties of the monocrystalline sheet during growth of the monocrystalline sheet in order to obtain "real time" information to determine if properties of the monocrystalline sheet are as desired.

However, there is a lack of techniques for measurement of properties of monocrystalline sheets during growth. Measurement is complicated by the fact that a crystalline sheet may be growing on or within a melt at an elevated temperature, which provides challenges to delivering a probe signal to the crystalline sheet and detecting a measurement signal with enough accuracy to properly monitor the growing sheet. It is with respect to these and other considerations that the present improvements have been needed.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, an apparatus to monitor thickness of a crystalline sheet grown from a melt may include a process chamber configured to house the melt and the crystalline sheet; an x-ray source disposed on a first side of the crystalline sheet and configured to deliver a first x-ray beam that penetrates a thickness of the crystalline sheet from a first surface to a second surface opposite the first surface; and an x-ray detector disposed on the first side of the crystalline sheet and configured to intercept a second x-ray beam that is generated by reflection of the first x-ray beam from a group of crystallographic planes that extend through the thickness of the crystalline sheet, wherein $\lambda = 2d \sin \theta$, where $\lambda$ is a wavelength of at least some x-rays of the first x-ray beam, d is a spacing between adjacent crystallographic planes of the group of crystallographic planes, and $\theta$ is an angle of incidence of the at least some x-rays with respect to the group of crystallographic planes.

In another embodiment, an apparatus to control crystalline sheet grown from a melt may include a process chamber configured to house the melt and crystalline sheet and a thickness monitoring system that includes: an x-ray source configured to deliver a first x-ray beam that penetrates the crystalline sheet through a thickness of the crystalline sheet from a first surface to a second surface opposite the first surface; and an x-ray detector configured to intercept a second x-ray beam that is generated by Bragg diffraction of the first x-ray beam from a group of crystallographic planes that extend through the thickness of the crystalline sheet. The apparatus may also include a control system coupled to the detector and configured to receive a measurement signal from the detector indicative of a thickness of the crystalline sheet between the first surface and the second surface; and, responsive to the measurement signal, send at least one control signal to adjust at least one of: heating rate of the melt, cooling rate at a crystallization region of the melt, and pulling rate of the crystalline sheet.

In a further embodiment, a method for controlling thickness of a crystalline sheet may include crystallizing the crystalline sheet on a surface of a melt using a crystallizer wherein the crystalline sheet has an initial thickness downstream of the crystallizer; pulling the crystalline sheet away from the crystallization front along a pull direction; directing a first x-ray beam to the crystalline sheet, wherein the first x-ray beam is configured to penetrate the crystalline sheet through a thickness of the crystalline sheet from a first surface to a second surface opposite the first surface; and intercepting at an x-ray detector a second x-ray beam that is generated by Bragg diffraction of the first x-ray beam from a group of crystallographic planes that extend through the thickness of the crystalline sheet.

BRIEF DESCRIPTION OF THE DRAWINGS

FIG. 5A depicts a side view of an apparatus for monitoring sheet thickness according to further embodiments of the disclosure;

DETAILED DESCRIPTION

Figure 1:
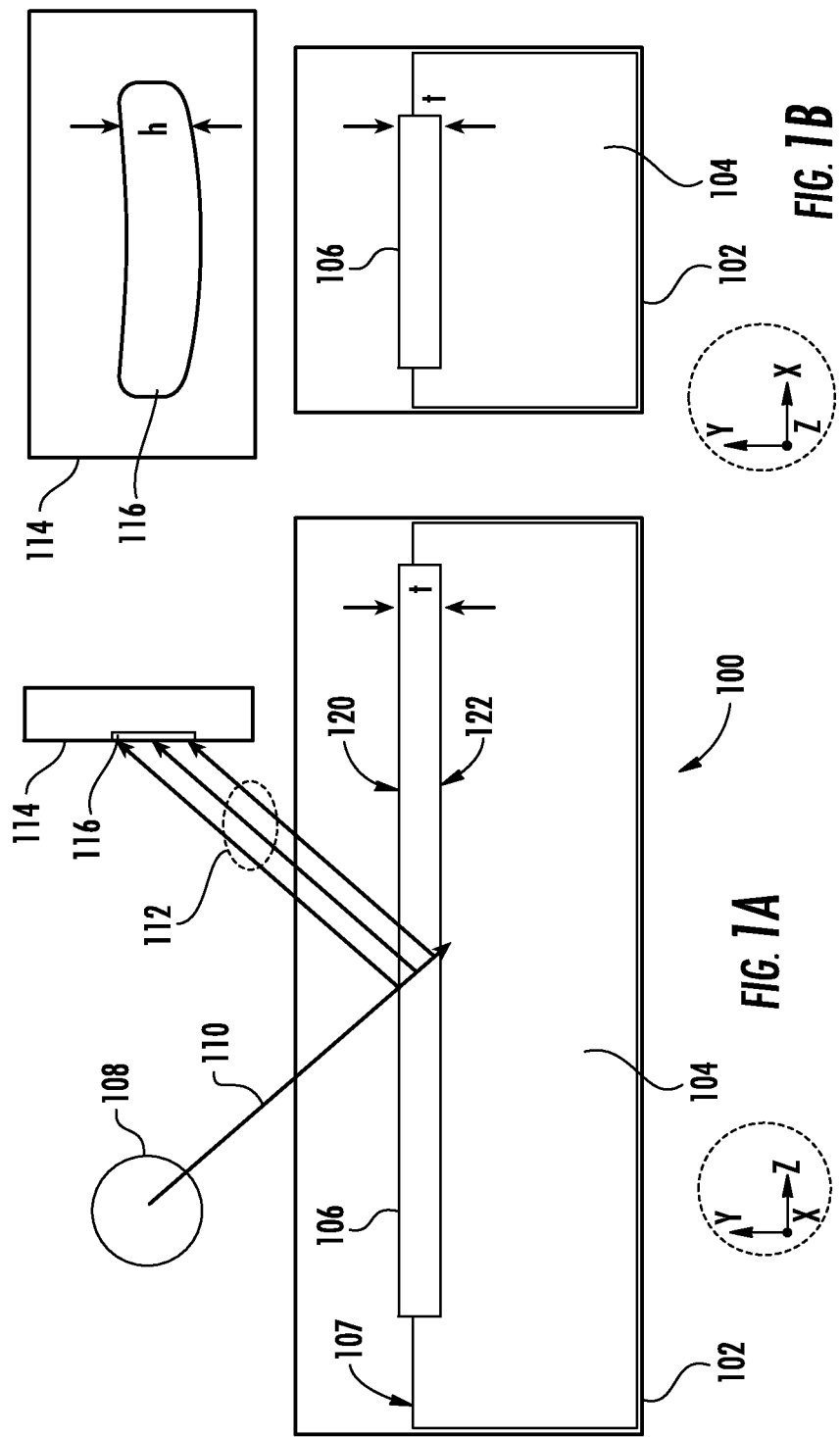
FIG. 1A depicts a side view of an apparatus for monitoring sheet thickness according to embodiments of the disclosure.
FIG. 1B depicts an end view of the apparatus of FIG. 1A.

The present embodiments will now be described more fully hereinafter with reference to the accompanying drawings, in which some embodiments are shown. The subject matter of the present disclosure, however, may be embodied in many different forms and should not be construed as limited to the embodiments set forth herein. Rather, these embodiments are provided so that this disclosure will be thorough and complete, and will fully convey the scope of the subject matter to those skilled in the art. In the drawings, like numbers refer to like elements throughout.

The present embodiments provide multiple advantages for monitoring and controlling thickness of a crystalline layer, including a crystalline layer that is grown from a melt. The present embodiments provide a non-contact thickness measurement approach using x-rays to probe a crystalline sheet. In various embodiments the thickness of a crystalline sheet may be monitored in-situ during growth of the crystalline sheet from a melt. In particular embodiments the monitoring of sheet thickness may be provided as part of a control system that may adjust in real-time at least one parameter of an apparatus for growing the crystalline sheet. For example, embodiments provide a melt growth apparatus in which a crystalline sheet is drawn from the melt by control of components that heat the melt, cool the melt at the melt surface to initiate crystallization of a crystalline sheet, and draw the crystalline sheet from the melt in order to fabricate a crystalline sheet of desired dimensions. In some embodiments, specialized heaters may be employed to melt back a portion of the crystalline sheet as it is being drawn. Various embodiments may provide real-time thickness information of the crystalline sheet, which may be used to adjust parameters for heating the melt, crystallizing the crystalline sheet, pulling or drawing the crystalline sheet, and melting back the crystalline sheet. In particular embodiments, the adjustment to parameters may be performed during sheet growth so that sheet thickness is dynamically controlled by probing a growing crystalline sheet with x-rays and adjusting parameters of the growth apparatus as needed.

In various embodiments an x-ray source and x-ray detector are arranged with respect to a crystalline sheet in order to detect an image of the crystalline sheet using Bragg diffraction as detailed below. The present embodiments take advantage of the fact that x-rays have wavelike characteristics in which the x-rays have wavelengths comparable to the inter-atomic spacing between planes of atoms within a crystalline material, which are referred to herein as "crystallographic planes." Accordingly, when x-rays impinge upon a crystalline surface, certain wavelengths may reflect from the planes of atoms in a manner that generates patterns of constructive interference analogous to optical diffraction gratings. This process is known as x-ray diffraction and involves the constructive interference of x-ray photons reflected from different crystallographic planes, which produces a diffraction pattern characterized by peaks in x-ray intensity where the constructive interference occurs. The Bragg law or Bragg equation (Eq. 1 below) establishes the relationship between x-ray wavelength, an angle of incidence of x-rays with respect to a crystallographic plane, and the spacing between successive crystallographic planes, for which constructive interference takes place:

$$\lambda = 2d \sin \theta \quad (1)$$

where $\lambda$ is a wavelength x-rays, d is an interplanar spacing between adjacent crystallographic planes of a group of crystallographic planes, and $\theta$ is a second angle of incidence of the x-rays with respect to the group of crystallographic planes.

In various embodiments, an x-ray source and x-ray detector are arranged to form an image of a beam of x-rays that are generated by Bragg diffraction (x-ray diffraction) from x-rays incident upon a crystalline sheet. The x-ray source and x-ray detector are arranged such that the x-ray detector measures a thickness of the crystalline sheet according to a height of an image formed by select x-rays whose angle of incidence and wavelength satisfy the Bragg equation for a given set of crystallographic planes of the crystalline sheet. As detailed below, the x-ray source may be arranged to provide x-rays of a suitable wavelength configured to penetrate the entire thickness of the crystalline sheet being measured. In this manner, x-ray photons may be reflected from a given set of parallel crystallographic planes that extend throughout the thickness of the crystalline sheet. Because the given set of crystallographic planes satisfy the Bragg equation, constructive interference leads to a peak in x-ray intensity registered by the x-ray detector that extends for a distance that is proportional to the thickness of the crystalline sheet.

Thus, the height of the x-ray image formed at the x-ray detector may be used as a direct measure of sheet thickness of the crystalline sheet. A particular advantage of the apparatus of the present embodiments is that sheet thickness of a crystalline sheet may be accurately measured even when that sheet is immersed within or in contact with a melt, because the apparatus is configured to detect solely a predetermined diffraction signal from the crystalline sheet. In particular, although x-rays that are directed to a crystalline sheet may strike and scatter from other material including the melt from which the crystalline sheet is grown, such x-rays are not scattered in a manner that satisfies the Bragg equation because the other material does not in general include crystallographic planes. Thus, solely x-rays scattered from the select group of crystallographic planes of the crystalline sheet are registered as an image at the x-ray detector. This provides a convenient approach for measuring sheet thickness in challenging environments, such as at high temperatures, and in circumstances in which the crystalline sheet may be disposed at or near a melt surface. In addition, changes in sheet thickness may be determined at a speed that is approximately that of the components of the x-ray detector, which may be on the order of milliseconds or less.

FIG. 1A depicts a side view of an apparatus 100 for monitoring sheet thickness according to embodiments of the disclosure. The apparatus 100 includes a process chamber 102 that may include various components (not separately shown) to contain a melt 104. As detailed below the melt 104 may be generated by known components such as resistance heaters that direct heat to the process chamber 102. In the example of FIG. 1A, the apparatus 100 is configured to generate a crystalline sheet 106 that is disposed at or near the surface 107 of the melt 104. The crystalline sheet 106 may be formed by generating a melt of a desired material, such as silicon or sapphire ($Al_2O_3$). For many applications, it may be desirable to form a sheet of monocrystalline material by careful crystallization of the material from a homogeneous melt. Thus, a crystalline sheet of silicon may be formed from a melt composed of silicon. In some applications, it may be desirable to generate thin crystalline sheets having thickness less than a few millimeters. For example, for many solar cell applications, silicon sheets having a thickness of 500 μm, 300 μm, 200 μm, 50 μm or less may be desirable. This may be accomplished by removing heat locally from the surface 107 of the melt 104 to initiate crystallization of a thin layer.

In particular embodiments in which the melt 104 is silicon, the crystalline sheet 106 may be crystallized at the surface 107 of the melt 104 by employing known components that remove heat near the surface 107, such as a crystallizer (not shown). In the case of crystalline silicon, the crystalline sheet 106 may float at the surface 107 such that the crystalline sheet 106 is mostly submerged within the melt 104. In addition, the melt temperature needed for drawing a crystalline sheet 106 from a melt of silicon (~1685 K) presents a challenging environment to measure properties of the crystalline sheet 106, such as sheet thickness. Moreover, it may be desirable to adjust processing conditions during formation of the crystalline sheet 106 in order to adjust the thickness of the crystalline sheet 106.

The apparatus 100 provides the ability to monitor the thickness of a crystalline sheet 106 in real time during growth of the crystalline sheet 106 in the environment of the melt 104. In particular, the apparatus 100 includes an x-ray source 108 that is positioned on a first side (outer side) of the crystalline sheet 106. The x-ray source 108 is configured to generate x-rays, shown in FIG. 1A as the x-ray beam 110, which impinges upon the crystalline sheet 106. Although the x-ray beam 110 is illustrated as a single ray, the x-ray beam 110 includes multiple x-ray photons, which may form a diverging beam in some examples, or may be composed of x-rays having parallel trajectories in other examples. As shown in FIG. 1A, the x-ray beam 110 is configured to penetrate through the entire thickness t between an upper surface 120 and lower surface 122 of the crystalline sheet 106 as defined along the direction parallel to the Y-axis of the Cartesian coordinate system shown. Because the x-ray beam 110 is composed of multiple x-ray photons that have wavelike properties, different photons may reflect from different crystallographic planes within the crystalline sheet 106 as the x-ray beam 110 penetrates the crystalline sheet 106. As discussed in more detail with respect to FIG. 2, the angle of incidence of x-ray beam 110 may be configured to generate constructive interference that corresponds to a Bragg diffraction peak for a select set of crystallographic planes within the crystalline sheet 106. This may result in the generation of a reflected (diffracted) x-ray beam, shown as the x-ray beam 112. The x-ray beam 112 is composed of x-rays that satisfy the Bragg equation (Eq. (1) for a select crystallographic plane within the crystalline sheet 106. As shown in FIG. 1A, the x-ray beam 112 is composed of multiple x-rays that satisfy the Bragg equation and are reflected from different planes of atoms within the crystalline sheet 106. These multiple x-rays are mutually parallel to one another. Because the crystalline sheet 106 has a finite thickness, such as 1 mm, the multiple x-rays that are contained in the x-ray beam 112 may impinge upon an x-ray detector 114 that is positioned on the same side of the crystalline sheet 106 as the x-ray source 108, forming an image that is proportional to the finite thickness.

As more clearly illustrated in FIG. 1B the x-ray detector 114 may therefore generate an image 116 of the x-ray beam 112 in which a height h of the image 116 is proportional to the thickness t of the crystalline sheet 106, where a proportionality constant may be calculated from simple geometrical calculation. In this instance, with the incident and reflected angles being equal, h=2t.

In accordance with various embodiments, the position and orientation of the x-ray source 108, as well as position and orientation of the x-ray detector 114 may be adjusted to capture an image of the crystalline sheet 106 based upon a select crystallographic plane that is inherent in the material of the crystalline sheet 106. For example, crystalline silicon has a face-centered cubic (more particularly, fcc diamond) structure that is defined by various crystallographic planes oriented along different directions. When silicon crystalline sheets are grown from a melt, a frequent goal is to form single crystalline (monocrystalline sheet) sheet that is to be used to form multiple monocrystalline silicon substrates. For example, the crystalline sheet 106 may be a monocrystalline silicon sheet having a (100) orientation in which (100) crystallographic planes (the notations of crystallographic planes used herein are based upon Miller index convention) are oriented parallel to the surface 107, and lie within the x-z plane as shown. In order to detect an x-ray image of the crystalline sheet 106 in this example, the x-ray source 108 and x-ray detector 114 may be positioned to generate x-rays and capture x-rays that satisfy the Bragg equation when reflected from the crystallographic planes that are parallel to the (100) crystallographic plane, as detailed below.

Figure 2:
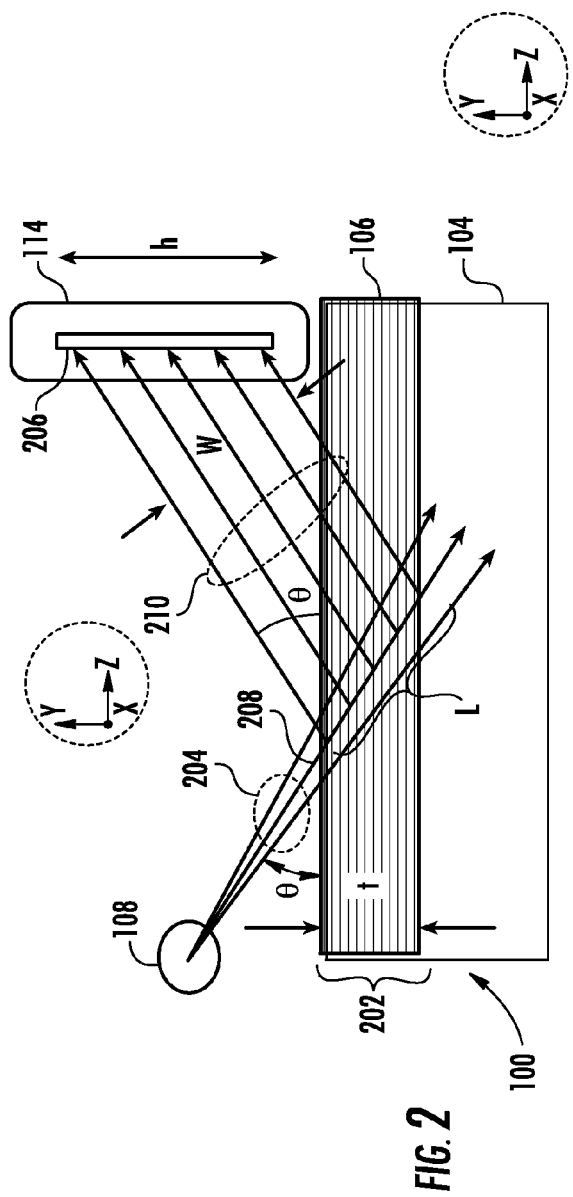
FIG. 2 depicts details of the geometry for monitoring sheet thickness using the apparatus of FIG. 1A.

Turning now to FIG. 2 there are shown details of the geometry of the apparatus 100 that illustrate the geometrical relation between crystallographic planes in the crystalline sheet 106, x-ray source 108, and x-ray detector 114 that may be used to form the image 116. In this example, it may be assumed that the crystalline sheet 106 is composed of monocrystalline silicon having a (100) orientation. As will be readily appreciated by those of ordinary skill in the art, a group of (100) crystallographic planes extends throughout the thickness t of the crystalline sheet 106. It will be further appreciated by those of ordinary skill in the art that a set of (400) crystallographic planes that are parallel to the (100) crystallographic planes (lie within the x-z plane) generate strong Bragg diffraction peaks for materials having the crystal structure of silicon (fcc diamond), which are illustrated as the set of planes 202 in FIG. 2. In the example of FIG. 2, the x-ray source 108 may direct x-ray beam 204 to the crystalline sheet 106, where the x-ray beam 204 includes x-rays having a target wavelength $\lambda_T$. Accordingly, an image 206 of the crystalline sheet 106 may be formed at the x-ray detector 114 when x-rays having the target wavelength $\lambda_T$ are provided at an angle of incidence θ with respect to the set of (100) (or (400)) crystallographic planes, where $$\lambda_T = 2d_{(400)} \sin \theta \qquad (2)$$

where $d_{400}$ is the spacing between adjacent (400) planes.

In particular, the x-rays of x-ray beam 204 that are incident at the angle of incidence θ and have a target wavelength $\lambda_T$ are reflected from (400) crystallographic planes at an angle of reflection also equal to θ. These x-rays that satisfy the Eq. (2) are represented by the ray 208 and may be composed of multiple x-ray photons that penetrate throughout the crystalline sheet 106. These x-ray photons are reflected from the (400) planes to generate constructive interference that causes a peak in radiation intensity of x-rays to be detected at x-ray detector 114. More particularly an x-ray beam 210 is reflected from the crystalline sheet 106, where the x-ray beam 210 is composed of parallel x-rays having the same wavelength. The beam width W of the x-ray beam 210 is determined by the path length L of the ray 208 within the crystalline sheet 106. In other words, in this example, the x-ray beam 210 results from the reflection of individual x-ray photons that reflect from myriad different (400) planes that extend through the thickness of the crystalline sheet 106. The myriad different (400) planes represent reflecting surfaces within the crystalline sheet 106, which may reflect x-rays that constructively interfere and form a Bragg peak that constitutes the x-ray beam 210.

Accordingly, for a given angle of incidence θ the path length L and beam width W are fixed for a given thickness t of the crystalline sheet 106. When the x-ray beam 210 strikes the x-ray detector this beam width W is detected as a height h of the image 206 as shown. Moreover, the path length L and therefore beam width W of the x-ray beam 210 vary as the thickness t of crystalline sheet 106. The change in beam width W may therefore be detected as a change in height h.

As will be readily appreciated from FIG. 2, the height h of the image 206 may be comparable, but somewhat larger than the thickness t of the crystalline sheet 106. For measurement of exemplary sheet thickness in the range of for example, 50 μm to 2 mm, the height h may be conveniently detected by known x-ray detectors, which may have a planar detector surface. Moreover, the height information may be captured electronically, may be stored, and may be transmitted to other devices in order to monitor or control sheet thickness of the crystalline sheet 106.

Figure 3:
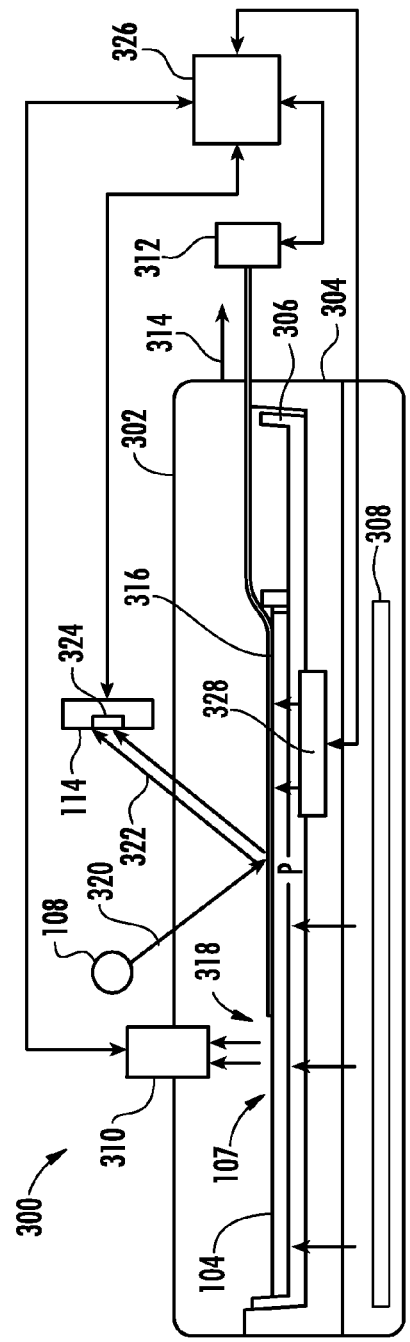
FIG. 3 depicts a system for controlling sheet thickness according to additional embodiments of the disclosure.

FIG. 3 depicts a system 300 for controlling sheet thickness according to additional embodiments of the disclosure. The system 300 includes a process chamber 302, which may be configured to heat a material to form a melt and to extract a crystalline sheet from the melt. In various embodiments, the process chamber 302 may include an outer wall, insulation, crucible holder, crucible, heater, crystallizer, crystal puller, and other known components that are used to crystallize a crystalline sheet from a melt. In the example depicted in FIG. 3 the process chamber 302 includes a crucible holder 304, crucible 306, and heater 308, which is used to provide heat (shown as vertical arrows) to the crucible 306 and to form the melt 104. The process chamber 302 also includes a crystallizer 310, which may be a known device that removes heat from a portion of the melt 104, particularly at the surface 107. This may result in the crystallization of a portion of the melt 104. The crystallization may be initiated by a crystalline seed (not shown), which may be drawn by a crystal puller 312 along a pull direction 314 that is parallel to the Z-axis. This causes the formation of a crystalline sheet 316 whose leading edge 318 may be adjacent the crystallizer 310. The process chamber 302 may also include a melt back heater 328 that provides heat to a portion of the crystalline sheet 316 to melt back a desired thickness of the crystalline sheet 316.

During the process for forming a crystalline sheet 316 using the system 300, the thickness of the crystalline sheet 316 may be monitored using the x-ray source 108 and x-ray detector 114, whose operation has been described herein above. The x-ray source 108 is arranged to direct an x-ray beam 320 to the crystalline sheet 316 at a point P downstream with respect to the crystallizer 310. An x-ray beam 322 that is generated by Bragg diffraction of the x-ray beam 320 is detected as an image 324 by the x-ray detector 114, from which the thickness of the crystalline sheet 316 may be determined as discussed above. The system 300 further includes a controller 326 that is configured to monitor and control formation of the crystalline sheet 316. The controller 326 may be embodied in hardware such as logic circuitry, software, or a combination of hardware and software. The controller 326 may be coupled to the x-ray detector 114, the crystallizer 310, crystal puller 312, and melt back heater 328.

In particular embodiments, the controller 326 may be configured to receive thickness information from the x-ray detector 114, and may generate control signals to at least one component of the system 300 based upon the thickness information. For example, the controller 326 may receive a measurement signal from the x-ray detector 114 that is indicative of a thickness t of the crystalline sheet 106 between the upper surface 120 and the lower surface 122 as discussed above. The measurement signal may be a single point thickness measurement at a given point on the crystalline sheet 106, or may represent an average thickness, range of thickness, thickness profile, or other measurement indicative of the thickness of crystalline sheet 106. When the measurement signal received from the x-ray detector 114 indicates that the thickness of the crystalline sheet 106 is to be adjusted, responsive to the measurement signal, the controller 326 may generate and send control signal(s) to the appropriate component or components of the system 300. For example, these control signals may adjust operation of a heating system such as the melt back heater 328, the crystallizer 310, the crystal puller 312 or any combination of these components.

In particular embodiments, the crystalline sheet 316 may be a monocrystalline silicon material in which the sheet thickness near the leading edge 318 may be 1-2 μm in some instances. However, it may be desirable for certain applications to produce a final sheet thickness in the range of 50 μm to 500 μm, for example. In one example, this may be accomplished by control of heat that is provided to the crystalline sheet 316 downstream of the crystallizer 310. For example, the melt back heater 328 may be configured to melt back a portion of the crystalline sheet 316 as it is drawn along the pull direction 314 to produce a final sheet thickness that corresponds to a target sheet thickness before the crystalline sheet 316 is withdrawn from the melt 104. Accordingly, the x-ray detector 114 may measure thickness information of the crystalline sheet 316 at the point P, which may, but need not, lie upstream of the melt back heater 328. When the thickness information is received by controller 326, the controller 326 may send a control signal to the melt back heater 328 to increase or decrease the amount of heat provided to the crystalline sheet 316 as it is drawn to the right over the melt back heater 328. In this manner the thickness of the crystalline sheet 316 that is reduced by melting may be increased or decreased to meet a target thickness.

In one example, the melt back heater 328 may initially be set to melt back a total thickness of 1 mm, while the target or final thickness of the crystalline sheet 316 is to be 200 μm. At a given instance the x-ray detector 114 may measure an image 324 that indicates a sheet thickness of 1.5 mm for the crystalline sheet 316 at the point P, just upstream of the melt back heater 328. Under the initial setting of the melt back heater 328, the total thickness reduction (1 mm) would generate a final thickness of 500 μm. Accordingly, when the controller 326 receives this thickness information, the controller 326 may send a control signal to the melt back heater 328 to increase heat flow to the crystalline sheet 316, and thus melt back a greater thickness (1.3 mm) to meet the target thickness (200 μm).

In other examples, the controller 326 may send control signals to the crystal puller 312 to adjust pull rate of the crystalline sheet 316 in order to adjust the melt back rate of the crystalline sheet responsive to measurement signals received from the x-ray detector 114. In still further examples, the controller 326 may send control signals to the crystallizer 310 to adjust the rate of heat removal from the melt 104, which may change the initial thickness of the crystalline sheet 316.

It is to be noted that Bragg reflection of an incident x-ray beam as it traverses through a crystalline layer may result in excessive attenuation of the x-ray beam through a process known as "kinematic extinction." This process may particularly apply for longer wavelengths of x-rays and for larger interplanar spacings between crystallographic planes. In addition, the mass attenuation coefficient of a given material of a crystalline sheet to be measured may be sufficiently large that little of no x-rays penetrate to the bottom of a crystalline sheet. In order to ensure that sufficient x-rays penetrate a crystalline sheet to generate a reflected beam that provides an image of the entire sheet thickness, various embodiments address this problem in different manners.

In one example, the wavelength of an incident x-ray beam may be reduced to reduce the mass attenuation. For example, an x-ray beam may be generated using a monochromatic source of X-rays. Table I. provides a listing of wavelengths of some common x-ray sources as well as the Bragg angle ($\theta$) for various crystallographic planes of silicon at the different wavelengths.

TABLE I

| | | | | Xray target/Kα wavelength (A) | | | | | |
|---|---|---|---|---|---|---|---|---|---|
| | | | | W | Mo | Cu | Co | Fe | Cr |
| | | | | 0.21 | 0.71 | 1.54 | 1.79 | 1.94 | 2.29 |
| h | k | l | d (A) | | | theta (deg) | | | |
| 1 | 1 | 1 | 3.15 | 1.92 | 6.48 | 14.18 | 16.53 | 17.93 | 21.35 |
| 2 | 2 | 0 | 1.93 | 3.13 | 10.63 | 23.58 | 27.68 | 30.18 | 36.47 |
| 3 | 1 | 1 | 1.64 | 3.67 | 12.49 | 27.98 | 33.01 | 36.12 | 44.19 |
| 4 | 0 | 0 | 1.36 | 4.43 | 15.12 | 34.46 | 41.07 | 45.31 | 57.21 |
| 3 | 3 | 1 | 1.25 | 4.83 | 16.51 | 38.07 | 45.72 | 50.78 | 66.37 |
| 4 | 2 | 2 | 1.11 | 5.43 | 18.63 | 43.86 | 53.57 | 60.54 | |
| 3 | 3 | 3 | 1.05 | 5.76 | 19.80 | 47.31 | 58.58 | 67.45 | |
| 5 | 1 | 1 | 1.05 | 5.76 | 19.80 | 47.31 | 58.58 | 67.45 | |
| 4 | 4 | 0 | 0.96 | 6.27 | 21.64 | 53.15 | 68.29 | | |

As illustrated, the wavelength of Cu Kα is 1.54 Å, while the wavelength of Mo Mo Kα is 0.71 Å, and the wavelength of W Kα is 0.21 Å. As also shown in Table I. the Bragg angle for Mo Kα, for example, is smaller than that of Cu Kα. For example, in consideration of the (400) plane, $\theta$ for Mo Kα is 15.12 degrees, and for Cu Kα is 34.46 degrees. Thus, use of Mo Kα radiation may increase the path length of an x-ray beam within a crystalline sheet because the x-ray beam traverses the crystalline sheet at a more glancing angle of incidence. However, this may be compensated for by a reduction in mass attenuation by the silicon sheet due to the lower wavelength of Mo Kα radiation.

Figure 4:
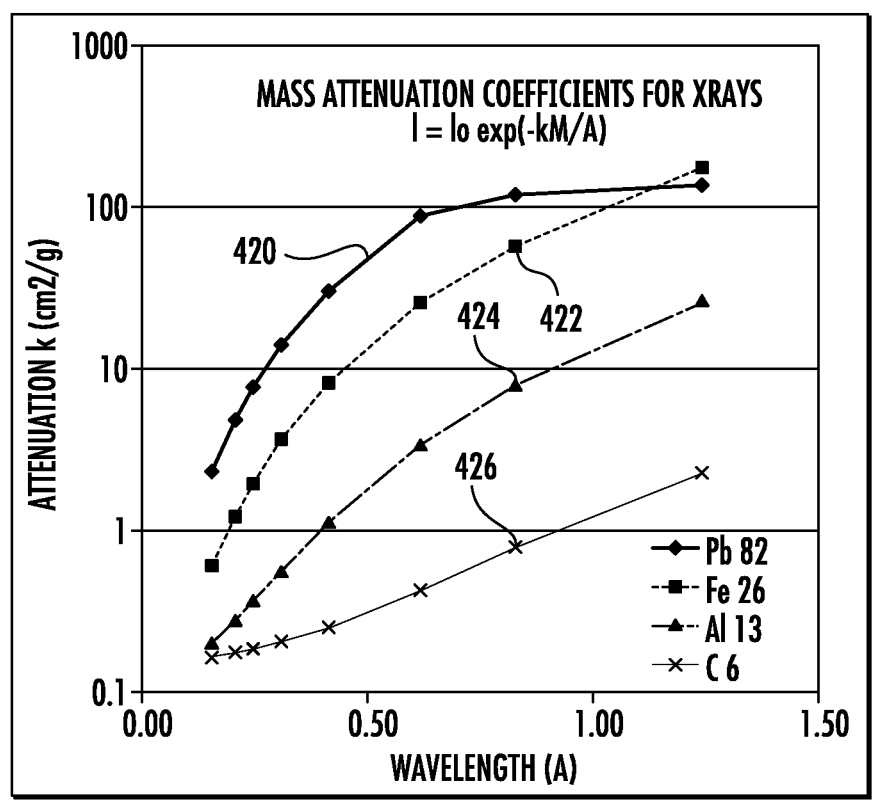
FIG. 4 depicts X-ray attenuation as a function of wavelength for various materials.

Referring now to FIG. 4 there is shown a graph that illustrates mass attenuation as a function of x-ray wavelength for several common materials including Pb (curve 420), Fe (curve 422), Al (curve 424) and C (curve 426). Silicon exhibits mass attenuation similar to that of Al. As may be apparent from consideration of curve 424, Cu Kα K radiation at 1.54 Å may result in a value of approximately 80 cm$^2$/g while Mo Kα K radiation at 0.71 Å generates a value of approximately 5 cm$^2$/g. Based on these values, for a 1 mm silicon sheet thickness the crystalline sheet absorbs approximately 50% of incident radiation at the 0.71 Å wavelength, while nearly all the radiation is absorbed at 1.54 Å. Accordingly, a Mo Kα radiation source may be employed in circumstances in which sheet thickness cannot practically be measured by using longer wavelength sources such as Cu Kα K radiation.

Figure 5C:
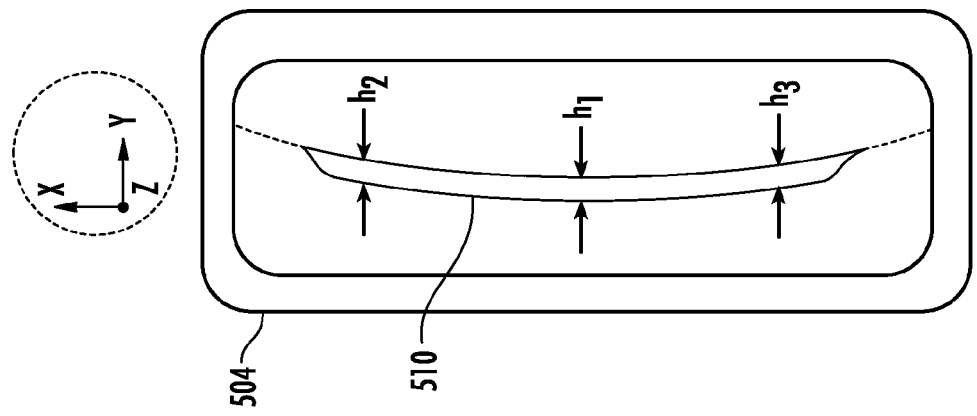
FIG. 5C depicts an end view of a detector of the apparatus of FIG. 5A.
Figure 5B:
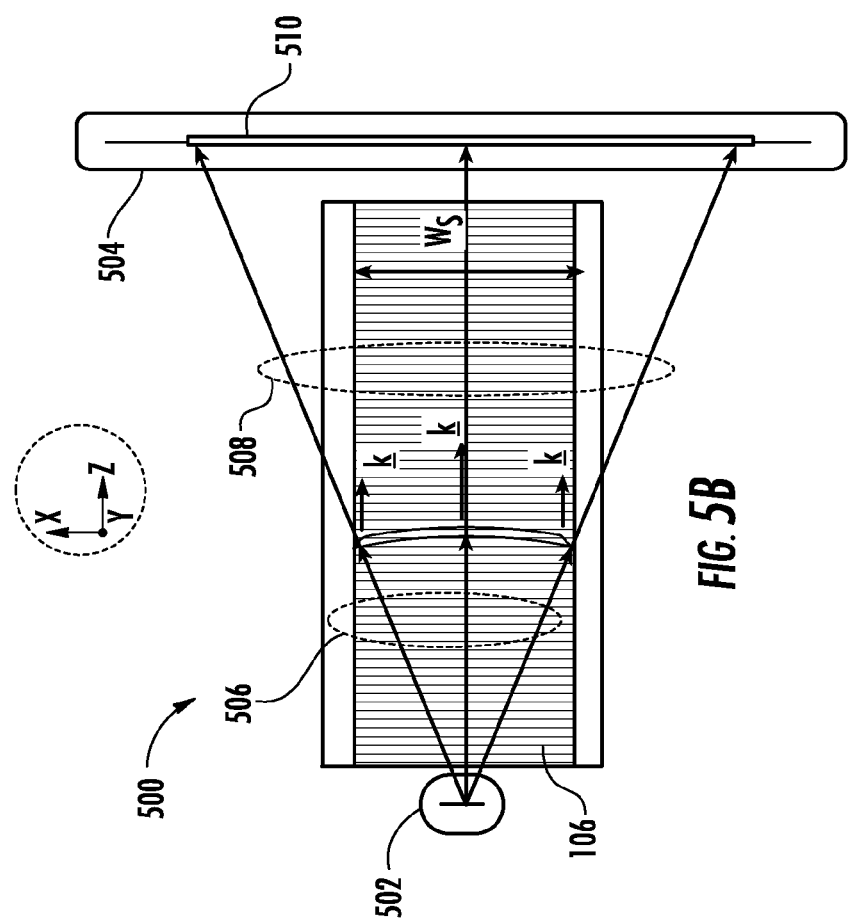
FIG. 5B depicts a top view of the apparatus of FIG. 5A.

In additional embodiments, the position of an x-ray source and x-ray detector may be adjusted to provide a more vertical angle of incidence for an x-ray beam that is directed to a crystalline sheet. This may provide the advantage that the path length of x-rays to completely penetrate a crystalline sheet is less than at more grazing incidence. FIG. 5A depicts a side view of an apparatus 500 for monitoring sheet thickness according to further embodiments of the disclosure. In this embodiment, the incident radiation makes an angle $\phi$ with the surface of the crystal, the reflected radiation makes an angle $\Psi$ with the surface, and the detector is positioned at right angles to the reflected radiation. This geometry leads to an image height h on the detector proportional to the thickness t of the crystal, given by the relationship h=t sin($\phi$+$\Psi$)/sin $\phi$. FIG. 5B depicts a top view of the apparatus of FIG. 4A; while FIG. 5C depicts an end view of a detector of the apparatus of FIG. 5A. In the apparatus 500 an x-ray source 502 is arranged to direct an x-ray beam 506 to the crystalline sheet 106 at a more vertical angle of incidence with respect to that provided by x-ray source 108 in FIG. 2. In the example of FIG. 4A, the x-ray source 502 may in some instances generate x-rays in x-ray beam 506 having a same or similar wavelength to that of x-ray beam 204. In this case, the Bragg condition may be satisfied by a crystallographic plane having a non-zero angle with respect to the upper surface 120 of the crystalline sheet 106.

Continuing with the example in which the crystalline sheet 106 is a monocrystalline sheet having (100) planes parallel to the upper surface 120, the x-ray beam 506 may form an angle of incidence $\phi$ with respect to the upper surface 120 (x-z plane). The x-ray beam 506 may also form an angle of incidence $\theta$ with respect to the crystallographic planes 514 that satisfies the Bragg equation, such that the x-ray beam 506 is diffracted by the crystallographic planes 514 to form a reflected beam, shown as the x-ray beam 508. For example, the crystallographic planes 514 may represent the (311) crystallographic planes of silicon, which form an angle of 25.2 degrees with respect to the (100) (or (400)) crystallographic planes. For this reason, the angle of incidence ($\phi$) with respect to the upper surface 120 of x-ray beam 506 is much steeper than that of x-ray beam 204. As noted, this provides a shorter path length L2 through the crystalline sheet 106 and allows the x-ray detector 504 to more conveniently intercept the x-ray beam 508, to form the image 510.

As further illustrated in FIG. 5B and FIG. 5C, the image 510 formed by the x-ray beam 508 is a two dimensional image. As particularly shown in FIG. 5B the x-rays of x-ray beam 506 may diverge such that the x-ray beam 506 intercepts the crystalline sheet 106 along its entire width Ws and is reflected as the x-ray beam 508 to form the image 510. As will be readily appreciated by those of ordinary skill in the art, the image 510 represents a portion of a diffraction cone of which the x-ray beam 508 forms a portion. This cone has an axis normal (perpendicular) to the diffraction plane, an apex located at the position of the image of the Xray source reflected in the diffraction plane and an angle of ($\pi$–$\theta$). Accordingly, the image 510 may exhibit some elliptical curvature that represents the intersection of a diffraction cone with a planar surface, as illustrated in FIG. 5C. As further shown in FIG. 5C, the height (along the Y-axis) of the image 510 may be measured at various points along the x-axis. FIG. 5C also illustrates three different height measurements, $h_1$, $h_2$, and $h_3$. The values of these measurements may vary according to a thickness variation of the crystalline sheet along the direction parallel to the X-axis. Accordingly, a thickness profile, average thickness, thickness variation, or other information, may be extracted from the image 510, either by the x-ray detector 504 or by a controller coupled to the x-ray detector 504, such as the controller 326. In some embodiments, this information may be employed by a controller to provide more fine control of components to adjust the thickness of the crystalline sheet 106.

In additional embodiments, the position of an x-ray source and x-ray detector may be configurable such that the angle of incidence of x-rays directed to a crystalline sheet may be varied. For example, in some embodiments the geometry illustrated in FIG. 2 and FIG. 5A may be provided by a single apparatus. This provides flexibility to tailor measurement according to sheet thickness range, crystallographic orientation of the sheet, or other factors, which may favor a more glancing angle of incidence of more steep angle of incidence in different instances.

Figure 6:
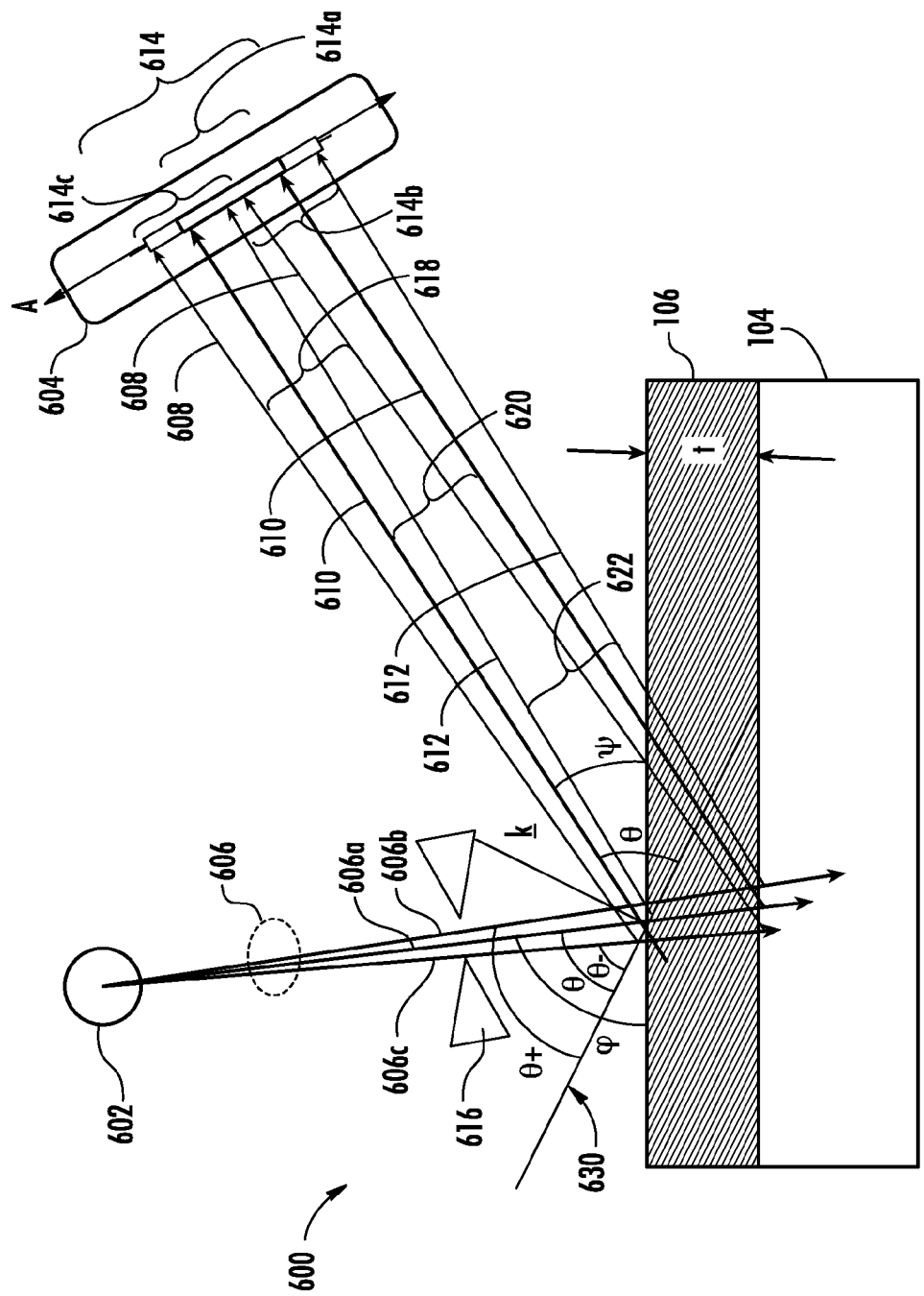
FIG. 6 depicts a side view of an apparatus for monitoring sheet thickness according to additional embodiments of the disclosure.

It is to be noted that a crystalline sheet need not be illuminated by monochromatic x-rays in order to generate an x-ray image based upon Bragg diffraction. For example, a polychromatic x-ray source may be employed as illustrated in FIG. 6. In particular, FIG. 6 shows an apparatus 600 that includes a polychromatic source, x-ray source 602, which may employ Brehmstrahlung radiation over a wavelength continuum to generate the x-ray beam 606. The x-ray beam 606 may pass through a collimation aperture 616 before striking the crystalline sheet 106. This may provide an intense beam over a range of wavelengths to the crystalline sheet 106. In one example, the x-ray source 602 and x-ray detector 604 may be arranged to generate an x-ray beam that forms an angle of incidence with respect to the crystallographic plane 630 that satisfies the Bragg equation for a target x-ray wavelength within the range of wavelengths generated in the x-ray beam 606. The crystallographic plane 630 may be, for example, the (311) plane of silicon, or other convenient crystallographic plane to be measured. In the case in which the collimation aperture 616 generates a parallel beam of x-rays, all x-ray photons within the x-ray beam 606 that have the target wavelength to meet the Bragg equation for the crystallographic plane 630 may diffract from within the crystalline sheet 106 and may be reflected to the x-ray detector 604.

However, in some implementations the collimation aperture 616 may accept and transmit x-rays over a narrow range of angles, such that the x-ray beam 606 impinges upon the crystallographic plane 630 over a range of angles. Because the x-ray beam 606 includes x-rays of multiple wavelengths, the Bragg equation is satisfied at different angles of incidence with respect to the crystallographic plane 630. Therefore x-ray photons having different initial trajectories, as well as energies, may all diffract from the crystallographic plane 630. In FIG. 6 there are shown three different x-ray beamlets that illustrate this phenomenon. The x-ray beam 606 in particular includes an x-ray beamlet 606a, an x-ray beamlet 606b, and x-ray beamlet 606c, each of which has a different trajectory, and each of which passes through the collimation aperture 616 to impinge upon the crystallographic plane 630 at a slightly different angle. The angle of the middle beamlet, x-ray beamlet 606a, is shown as forming an angle θ with respect to the crystallographic plane 630. In the example of FIG. 6 the wavelength of the x-ray beamlet 606a is configured to meet the Bragg equation for crystallographic plane 630 at the angle θ. Accordingly, the x-ray beamlet 606a is diffracted from the crystalline sheet 106 throughout its thickness, and forms a reflected beam shown as x-ray beamlet 610, whose outer two rays are illustrated. The x-ray beamlet 610 has a width 620 that is proportional to the thickness t of the crystalline sheet as discussed above with respect to FIG. 2. Accordingly, the x-ray beamlet 610 impacts a portion 614a of an image 614 at the x-ray detector 604.

On the other hand, the x-ray beamlet 606b forms an angle θ+ with respect to the crystallographic plane 630. In the example of FIG. 6 the wavelength of the x-ray beamlet 606b is configured to meet the Bragg equation for crystallographic plane 630 at the angle θ+. Accordingly, the x-ray beamlet 606b is diffracted from the crystalline sheet 106 throughout its thickness, and forms a reflected beam shown as x-ray beamlet 612, whose outer two rays are illustrated. The x-ray beamlet 612 has a width 622 that is proportional to the thickness t of the crystalline sheet as discussed above with respect to FIG. 2. Accordingly, the x-ray beamlet 612 impacts a portion 614b of an image 614 at the x-ray detector 604. Because of the different diffraction angle as compared to x-ray beamlet 610, the portion 614b is displaced on the x-ray detector 604 with respect to portion 614a.

Moreover, the x-ray beamlet 606c forms an angle θ− with respect to the crystallographic plane 630. In the example of FIG. 6 the wavelength of the x-ray beamlet 606c is configured to meet the Bragg equation for crystallographic plane 630 at the angle θ−. Accordingly, the x-ray beamlet 606c is diffracted from the crystalline sheet 106 throughout its thickness, and forms a reflected beam shown as x-ray beamlet 608, whose outer two rays are illustrated. The x-ray beamlet 608 has a width 618 that is proportional to the thickness t of the crystalline sheet as discussed above with respect to FIG. 2. Accordingly, the x-ray beamlet 608 impacts a portion 614c of an image 614 at the x-ray detector 604.

In sum the overlapping images, i.e. portion 614a, portion 614b, and portion 614c form the image 614. The image 614 may be less well defined that an image formed from monochromatic x-rays, since the image intensity may vary, for example, along the direction A. However, it may still be possible to determine thickness of the crystalline sheet 106 from the image 614 provided proper knowledge of the angular spread of the x-ray beam 606. In view of the above, it may be appreciated that a tradeoff may exist between increased x-ray intensity that may be generated from a polychromatic x-ray source and image quality of an image of a crystalline sheet, which may degrade when the x-ray beam provided by the polychromatic source is not sufficiently collimated.

In various embodiments an apparatus may be provided with enclosures that direct x-rays to and from a crystalline sheet to be measured. In particular, embodiments, the enclosures may be evacuated. This is advantageous for transport of x-rays over relatively long distances, such as several centimeters or several tens of centimeters, in which x-ray scattering from gas may be reduced by providing evacuated enclosures to conduct the x-ray to the crystalline sheet. Such evacuated enclosures also provide thermal insulation such that minimal disturbance to a furnace chamber or similar process chamber takes place.

Figure 7:
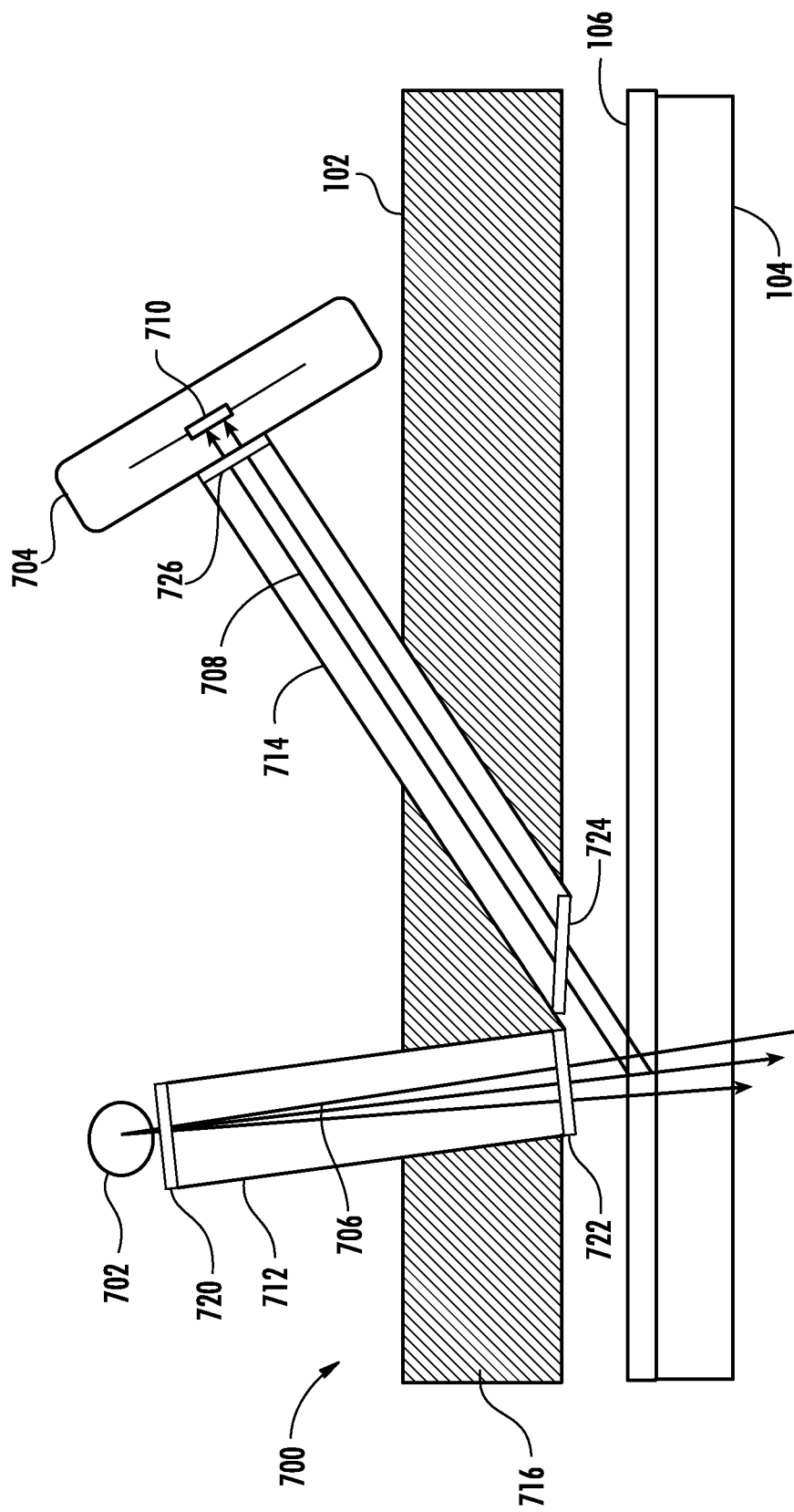
FIG. 7 depicts a side view of an apparatus for monitoring sheet thickness according to still further embodiments of the disclosure.

FIG. 7 depicts an apparatus 700 according to various additional embodiments. The apparatus 700 may include an x-ray source 702 and x-ray detector 704 that are configured, for example, as in the apparatus 500 or in the apparatus 100. The x-ray source 702 may generate an x-ray beam 706 that is diffracted from the crystalline sheet 106, forming the reflected x-ray beam, x-ray beam 708, which generates the image 710 on x-ray detector 704. The apparatus 700 includes an entrance enclosure 712 that is configured to conduct the x-ray beam 706 from the x-ray source 702 to the process chamber 102. The entrance enclosure 712 may be evacuated such that the x-ray beam 706 is conducted to the process chamber 102 under vacuum while traveling through the entrance enclosure 712. For example, a vacuum may correspond to a gas pressure ambient less than approximately $10^{-3}$ atmospheres ($<10^2$ Pa). As illustrated in FIG. 7, the entrance enclosure may extend into the process chamber 102, which may include insulation 716.

The apparatus 700 also includes an exit enclosure 714 configured to conduct the x-ray beam 708s from the process chamber 102 to the x-ray detector 704, which may also take place under vacuum. As illustrated in FIG. 7, the exit enclosure 714 may also extend into the process chamber 102. The entrance enclosure 712 may include a first entrance enclosure window 720 adjacent to the x-ray source 702 and a second entrance enclosure window 722 that is disposed within the process chamber 102. Similarly, the exit enclosure 714 may include a first exit enclosure window 724 disposed within the process chamber 102 and a second exit enclosure window 726 that is the adjacent to the x-ray detector 704. These windows may be configured to hold vacuum and to transmit x-rays. In one example, the second entrance enclosure window 722 and first exit enclosure window 724, which are each disposed within the process chamber 102, may be composed of material capable of withstanding high temperatures in which a melt 104 is housed, such as a silicon melt. Fused quartz or diamondlike carbon are examples of material that may be appropriate for use as the second entrance enclosure window 722 and first exit enclosure window 724. However, the embodiments are not limited in this context. The first entrance enclosure window 720 and second exit enclosure window 726 may be composed of the same material as used for second entrance enclosure window 722 and first exit enclosure window 724, although the temperature experienced by the first entrance enclosure window 720 and second exit enclosure window 726 may not need the use of such material.

In summary, the present embodiments provide the ability to measure thickness of a crystalline sheet or layer, including in challenging environments, such as in apparatus used to grow the crystalline sheet from a melt. Although the embodiments disclosed hereinabove provided examples that include measurement of silicon sheet growth from a melt, the present embodiments cover the measurement of other crystalline material such as sapphire sheets. Moreover, various embodiments may employ x-ray apparatus to measure crystalline sheets that are drawn vertically from a melt rather than horizontally as in the embodiments disclosed in the figures. Based upon present day x-ray detector technology, the present embodiments may be employed to measure thickness of a crystalline sheet to a resolution of less than 10 µm, which may satisfy requirements for producing thin silicon sheets for silicon photovoltaic applications.

Moreover, in various embodiments, the thickness of a crystalline sheet may be monitored in real time during growth of the crystalline sheet from a melt, and the thickness information may be used to adjust parameters that control crystalline sheet growth, thus providing a more robust crystalline sheet formation process.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Thus, the claims set forth below should be construed in view of the full breadth and spirit of the present disclosure as described herein.

What is claimed is:

1. An apparatus to monitor thickness of a crystalline sheet grown from a melt, comprising:
    a process chamber configured to house the melt and the crystalline sheet;
    an x-ray source disposed on a first side of the crystalline sheet and configured to deliver a first x-ray beam that penetrates a thickness of the crystalline sheet from a first surface to a second surface opposite the first surface; and
    an x-ray detector disposed on the first side of the crystalline sheet and configured to intercept a second x-ray beam that is generated by reflection of the first x-ray beam from a group of crystallographic planes that extend through the thickness of the crystalline sheet,
    wherein $\lambda = 2d \sin \theta$,
    where $\lambda$ is a wavelength of at least some x-rays of the first x-ray beam, d is a spacing between adjacent crystallographic planes of the group of crystallographic planes, and $\theta$ is an angle of incidence of the at least some x-rays with respect to the group of crystallographic planes.

2. The apparatus of claim 1, further comprising:
    a crucible configured to contain the melt;
    a heating system to provide heating to the melt;
    a crystallizer configured to generate a crystallization front of the crystalline sheet at a surface of the melt; and
    a crystal puller configured to draw the crystalline sheet at a pull rate along the surface of the melt.

3. The apparatus of claim 2, further comprising a controller configured to:
    receive a measurement signal from the detector indicative of the thickness of the crystalline sheet between the first surface and the second surface; and
    responsive to the measurement signal, send at least one control signal to adjust operation of at least one of: the heating system, crystallizer, and crystal puller.

4. The apparatus of claim 1, wherein the melt is silicon, and wherein a thickness of the crystalline sheet is less than 2 mm.

5. The apparatus of claim 1, wherein the x-ray source is configured to generate monochromatic radiation, wherein $\lambda$ is less than 1 Å.

6. The apparatus of claim 1, wherein the x-ray source is configured to generate polychromatic radiation.

7. The apparatus of claim 1, wherein the group of crystallographic planes is oriented at a non-zero angle with respect to the first surface.

8. The apparatus of claim 1, wherein the detector comprises a planar detector surface configured to form an x-ray image of the second x-ray beam, wherein a height of the x-ray image along a first direction of the planar detector surface is proportional to a thickness of the crystalline sheet between the first surface and second surface, and wherein a width of the x-ray image along a second direction of the planar detector surface is proportional to a width of the crystalline sheet.

9. The apparatus of claim 1, further comprising:
    an entrance enclosure configured to conduct the first x-ray beam from the x-ray source to the process chamber under vacuum; and
    an exit enclosure configured to conduct the second x-ray beam from the process chamber to the detector under vacuum.

10. An apparatus to control crystalline sheet grown from a melt, comprising:

a process chamber configured to house the melt and crystalline sheet;
a thickness monitoring system, comprising:
an x-ray source configured to deliver a first x-ray beam that penetrates the crystalline sheet through a thickness of the crystalline sheet from a first surface to a second surface opposite the first surface;
an x-ray detector configured to intercept a second x-ray beam that is generated by Bragg diffraction of the first x-ray beam from a group of crystallographic planes that extend through the thickness of the crystalline sheet; and
a control system coupled to the detector and configured to:
receive a measurement signal from the detector indicative of a thickness of the crystalline sheet between the first surface and the second surface; and
responsive to the measurement signal, send at least one control signal to adjust at least one of: heating rate of the melt, cooling rate at a crystallization region of the melt, and pulling rate of the crystalline sheet.

11. The apparatus of claim 10, further comprising:
a crucible configured to contain the melt;
a crystallizer configured to generate a crystallization front of the crystalline sheet at a surface of the melt, wherein the crystalline sheet has an initial thickness downstream of the crystallizer;
a melt back heater to melt back a fraction of the initial thickness; and
a crystal puller configured to draw the crystalline sheet at a pull rate along the surface of the melt, wherein the at least one control signal is operative to adjust operation of at least one of: the crystallizer, melt back heater, and crystal puller.

12. The apparatus of claim 10, wherein the x-ray source is configured to generate monochromatic radiation, wherein $\lambda$ is less than 1 Å.

13. The apparatus of claim 10, wherein the x-ray source is configured to generate polychromatic radiation.

14. The apparatus of claim 10, wherein the group of crystallographic planes is oriented at a non-zero angle with respect to the first surface.

15. The apparatus of claim 10, wherein the detector comprises a planar detector surface configured to form an x-ray image of the second x-ray beam, wherein a height of the x-ray image along a first direction of the planar detector surface is proportional to the thickness of the crystalline sheet between the first surface and second surface, and wherein a width of the x-ray image along a second direction of the planar detector surface is proportional to a width of the crystalline sheet.

16. The apparatus of claim 10, wherein the controller is configured to determine from the measurement signal at least one of: a single point thickness of the crystalline sheet, an average thickness of the crystalline sheet, a thickness profile of the crystalline sheet, and a thickness variation of the crystalline sheet.

17. The apparatus of claim 10, further comprising:
an entrance enclosure configured to conduct the first x-ray beam from the x-ray source to the process chamber under vacuum; and
an exit enclosure configured to conduct the second x-ray beam from the process chamber to the detector under vacuum.

18. A method for controlling thickness of a crystalline sheet, comprising:
crystallizing the crystalline sheet on a surface of a melt using a crystallizer wherein the crystalline sheet has an initial thickness downstream of the crystallizer;
pulling the crystalline sheet away from the crystallizer along a pull direction;
directing a first x-ray beam to the crystalline sheet, wherein the first x-ray beam is configured to penetrate the crystalline sheet through a thickness of the crystalline sheet from a first surface to a second surface opposite the first surface; and
intercepting at an x-ray detector a second x-ray beam that is generated by Bragg diffraction of the first x-ray beam from a group of crystallographic planes that extend through the thickness of the crystalline sheet.

19. The method of claim 18, further comprising:
forming an image of the second x-ray beam on the x-ray detector; and
determining a sheet thickness t of the crystalline sheet from a height h of the image, where h is proportional to t.

20. The method of claim 18, further comprising;
receiving a measurement signal indicative of the thickness of the crystalline sheet; and
sending a control signal to adjust one or more of: the crystallizing, the pulling, and melting back of the crystalline sheet.

* * * * *